United States Patent [19]
Kimura et al.

[11] Patent Number: 6,034,086
[45] Date of Patent: Mar. 7, 2000

[54] TRIFLUOROMETHYLQUINOLINECARBOXYLIC ACID DERIVATIVE

[75] Inventors: Tomio Kimura, Tokyo; Tetsushi Katsube, Ube; Takashi Nishigaki, Tokyo, all of Japan

[73] Assignees: Ube Industries, Ltd., Ube; Sankyo Company, Limited, Tokyo, Japan

[21] Appl. No.: 09/154,464

[22] Filed: Sep. 16, 1998

Related U.S. Application Data

[63] Continuation of application No. 08/776,083, filed as application No. PCT/JP95/01123, Jun. 7, 1995, abandoned.

[30] Foreign Application Priority Data

Jul. 18, 1994 [JP] Japan ..................... 6-165126

[51] Int. Cl.[7] ............... A61K 31/495; A61K 31/50; C07D 403/00; C07D 401/00

[52] U.S. Cl. ................ 514/255; 514/255; 514/254; 514/253; 544/224; 544/336; 544/358; 544/359; 544/360; 544/361

[58] Field of Search ................ 514/253, 254, 514/255; 544/336, 358, 359, 360, 361

[56] References Cited

U.S. PATENT DOCUMENTS

| | | | |
|---|---|---|---|
| 4,448,962 | 5/1984 | Irkura et al. | 544/362 |
| 4,544,658 | 10/1985 | Petersen et al. | 514/254 |
| 4,556,658 | 12/1985 | Grohe et al. | 514/254 |
| 4,563,459 | 1/1986 | Grohe et al. | 514/254 |
| 4,588,726 | 5/1986 | Petersen et al. | 514/254 |
| 4,668,680 | 5/1987 | Trehan et al. | 514/254 |
| 4,705,788 | 11/1987 | Schriewer et al. | 514/254 |
| 4,780,468 | 10/1988 | Bridges et al. | 514/312 |
| 4,822,801 | 4/1989 | Domagala et al. | 514/312 |
| 4,851,418 | 7/1989 | Sanchez | 514/300 |
| 5,221,676 | 6/1993 | Laborde et al. | 514/300 |
| 5,519,016 | 5/1996 | Kimura et al. | 514/212 |
| 5,587,386 | 12/1996 | Hayakawa et al. | 514/312 |

FOREIGN PATENT DOCUMENTS

| | | | |
|---|---|---|---|
| 304087 | 8/1988 | European Pat. Off. | |
| 305744 | 7/1989 | European Pat. Off. | |
| 470252 | 4/1990 | European Pat. Off. | |
| 394553 | 10/1990 | European Pat. Off. | |
| 470 252 | 2/1992 | European Pat. Off. | C07D 215/56 |
| 572 259 | 12/1993 | European Pat. Off. | |
| 62-187459 | 8/1987 | Japan . | |
| 63-104974 | 5/1988 | Japan . | |
| 64-66180 | 3/1989 | Japan . | |
| 1-125371 | 5/1989 | Japan . | |
| 2-231475 | 9/1990 | Japan . | |
| 89/06649 | 7/1989 | WIPO . | |
| WO 91/16894 | 11/1991 | WIPO . | |
| WO 9510519 | 4/1995 | WIPO . | |

OTHER PUBLICATIONS

Suto, Mark, et al., "Eluoroquinolones: Relationships between Structural Variations, Mammalian Cell Cytotoxicity, and Antimicrobial Activity", *J. Med. Chem.*, 35, 4745–4750 (1992).

Junko Nozaki–Renard et al., "A Fluoroquinolone (DR–3355) Protects Human Lymphocyte Cell Lines From HIV–1–Induced Cytotoxicity", *Aids*, 4, 1283–1286 (1990).

Sanchez et al., *J. Med. Chem.*, (1992), vol. 35, No. (2), pp. 361–367.

Klopman et al., *J. Med. Chem.*, (1993), vol. 37, No. (12), p. 2766.

Renau et al., *Antimicrob. Agents Chemother.*, (1996), vol. 40, No. (10), pp. 2363–2368.

Suto et al., *J. Med. Chem.*, (1992), vol. 35, No. (25), pp. 4745–4750.

*Primary Examiner*—S. Mark Clardy
*Assistant Examiner*—Sabiha N. Qazi
*Attorney, Agent, or Firm*—Frishauf, Holtz, Goodman, Langer & Chick, P.C.

[57] ABSTRACT

This invention relates to a 8-trifluoromethylquinolinecaboxylic acid derivative represented by the following formula (I):

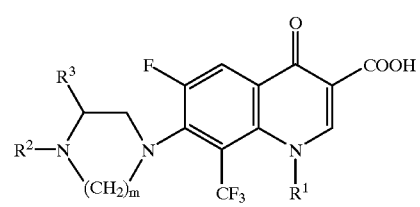

(I)

(wherein $R^1$ represents a lower alkyl group, a halogeno-lower alkyl group or a cycloalkyl group, $R^2$ represents a phenyl group which may be substituted by $R^0$, a 5-membered or 6-membered aromatic heteromonocyclic ring group containing 1 or 2 hetero atoms selected from N, O and S, which may be substituted by $R^0$, or an aromatic heterocyclic fused ring group in which the said aromatic heteromonocyclic ring group and a benzene ring are fused, $R^0$ represents a group selected from a halogen, a lower alkyl, a fluorine-substituted lower alkyl, a lower alkoxy or a lower alkylthio, $R^3$ represents hydrogen or a lower alkyl group, and m represents an integer of 2 or 3.) or a pharmaceutically acceptable salt thereof or an ester thereof.

25 Claims, No Drawings

TRIFLUOROMETHYLQUINOLINECARBOXYLIC ACID DERIVATIVE

This is a continuation of application Ser. No. 08/776,083 filed Jan. 17, 1997 (now abandoned), which is the United States designated application of International Application PCT/JP95/01123, filed Jun. 7, 1995.

TECHNICAL FIELD

This invention relates to a novel 8-trifluoromethylquinolinecarboxylic acid derivative which inhibits growth of human immunodeficient virus (hereinafter referred to as HIV), or a pharmaceutically acceptable salt thereof or an ester thereof.

BACKGROUND ART

HIV mainly infects $CD_4$-positive lymphocytes (helper/inducer), gradually reduces the number of the cells and finally causes severe acquired immunodeficiency syndrome (hereinafter referred to as AIDS). Many efforts have heretofore been made in order to treat AIDS, but development of vaccine is extremely difficult so that development of anti-viral agents has been expected. Though the anti-viral agents having inhibitory actions on a reverse transcriptase inherently possessed by the virus, which have been approved at present, have life-prolonging effects on AIDS patients, the agents cannot cure them completely. Further, these inhibiting agents have many problems that side effects such as myelopathy and digestive system disorder, etc. are severe, drug-resistant viruses are separated with high frequency from patients to whom the agent is administered for a long period of time, and others, whereby developments of novel chemicals and therapy using multiple agents in combination have been earnestly desired.

Recently, there has been reported the anti-HIV activity of DR-3355 which is an optical isomer of a synthetic antibacterial agent, Ofloxacin, having a quinolinecarboxylic acid skeleton (J. Nozaki, Renard et al., AIDS 4, 1283 (1990)). However, when the present inventors studied the cellular disorder-suppressing activity of DR-3355 to HIV-infected cells according to the method of R. Pauwel et al. described below, no anti-HIV activity was recognized. Also, there have been described the anti-HIV activities of Norfloxacin, Enoxacin, Ciprofloxacin, Lomefloxacin, Difloxacin, Tosufloxacin, etc. (WO 90/13542), but no anti-HIV activity was also recognized regarding these compounds.

The present inventors have studied about the anti-HIV activities of various kinds of quinolinecarboxylic acid derivatives and found that a quinolinecarboxylic acid derivative whose hydrophobicity is strengthened and whose antibacterial activity is weakened by introducing a trifluoromethyl group at 8-position and a cyclic diamine (e.g., a piperazinyl group or homopiperazinyl group which may be substituted) substituted by a phenyl group or an aromatic heterocyclic ring group at 7-position can specifically suppress growth of HIV in HIV-infected cells and further has an activity of suppressing a cytopathic effect (CPE) of HIV, in order to accomplish the present invention.

DISCLOSURE OF THE INVENTION

The present invention is a 8-trifluoromethylquinolinecarboxylic acid derivative represented by the following formula (I) or a pharmaceutically acceptable salt thereof or an ester thereof:

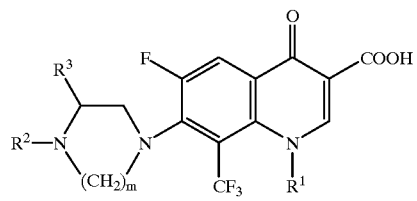

(wherein $R^1$ represents a lower alkyl group, a halogeno-lower alkyl group or a cycloalkyl group, $R^2$ represents a phenyl group which may be substituted by $R^0$, a 5-membered or 6-membered aromatic heteromonocyclic ring groups containing 1 or 2 hetero atoms selected from N, O and S, which may be substituted by $R^0$, or an aromatic heterocyclic fused ring group in which the said aromatic heteromonocyclic ring and a benzene ring are fused, $R^0$ represents a group selected from a halogen, a lower alkyl, a fluorine-substituted lower alkyl, a lower alkoxy or a lower alkylthio, $R^3$ represents a hydrogen or a lower alkyl group, and m represents an integer of 2 or 3.)

BEST MODE FOR PRACTICING THE INVENTION

As the lower alkyl group of $R^1$ in the above formula (I), there may be mentioned, for example, a $C_1$ to $C_4$ alkyl group such as methyl, ethyl, propyl, isopropyl, butyl, isobutyl, s-butyl and t-butyl, etc., preferably methyl, ethyl, propyl and isopropyl groups, particularly preferably methyl and ethyl groups.

As the halogeno-lower alkyl group of $R^1$, there may be mentioned, for example, a halogeno-$C_1$ to $C_4$ alkyl group such as fluoromethyl, chloromethyl, difluoromethyl, trifluoromethyl, 2-fluoroethyl, 2-chloroethyl, 2-bromoethyl, 2-iodoethyl, 2,2,2-trifluoroethyl, 3-fluoropropyl, 3-chloropropyl, 3-bromopropyl and 4-fluorobutyl, etc., preferably 2-fluoroethyl, 2-chloroethyl and 2,2,2-trifluoroethyl groups, particularly preferably a 2-fluoroethyl group.

As the cycloalkyl group of $R^1$, there may be mentioned, for example, a $C_3$ to $C_6$ cycloalkyl group such as cyclopropyl, cyclobutyl, cyclopentyl and cyclohexyl, etc., preferably cyclopropyl, cyclobutyl and cyclopentyl groups, particularly preferably a cyclopropyl group.

As the aromatic heteromonocyclic ring or aromatic heterocyclic fused ring group (hereinafter referred to as the aromatic heterocyclic ring group) of $R^2$, there may be mentioned, for example, 2-thienyl, 2-furyl, 2-oxazolyl, 2-thiazolyl, 2-imidazolyl, 2-, 3- or 4-pyridyl, 2-, 4- or 5-pyrimidinyl, 2-pirazinyl, 3-pyridazinyl, 2-benzoxazolyl, 2-benzothiazolyl and 2-benzoimidazolyl, preferably 2-thienyl, 2-furyl, 2-oxazolyl, 2-thiazolyl, 2-imidazolyl, 2-, 3- or 4-pyridyl, 2-, 4- or 5-pyrimidinyl, 2-pirazinyl and 3-pyridazinyl groups, particularly preferably 2-pyridyl and 2-pyrimidinyl groups.

As the substituent $R^0$ on the phenyl and the aromatic heterocyclic ring of $R^2$, there may be mentioned, for example, a halogen atom such as fluorine, chlorine, bromine, iodine, etc.; a $C_1$ to $C_4$ alkyl group such as methyl, ethyl, propyl, isopropyl, butyl, s-butyl, isobutyl and t-butyl, etc.; a fluorine-substituted $C_1$ to $C_4$ alkyl group such as mono-, di- or trifluoromethyl, 2-fluoroethyl, 2- or 3-fluoropropyl, 2-, 3- or 4-fluorobutyl, etc.; a $C_1$ to $C_4$ alkoxy group such as methoxy, ethoxy, propoxy, isopropoxy, butoxy, isobutoxy, s-butoxy and t-butoxy, etc.; and a $C_1$ to $C_4$ alkylthio group such as methylthio, ethylthio, propylthio, isopropylthio, butylthio, isobutylthio, s-butylthio and t-butylthio, etc., preferably fluorine, chlorine, methyl, ethyl, trifluoromethyl, methoxy, ethoxy, methylthio and ethylthio groups, particularly preferably fluorine, chlorine, methyl, trifluoromethyl, methoxy and methylthio groups.

As the lower alkyl group of $R^3$, there may be mentioned, for example, a $C_1$ to $C_4$ alkyl group such as methyl, ethyl, propyl, isopropyl, butyl, isobutyl, s-butyl and t-butyl, etc., preferably methyl, ethyl, propyl and isopropyl groups, particularly preferably methyl and ethyl groups.

The carboxyl group of the compound represented by the above formula (I) may be protected by a protective group to be an ester. As such a protective group, there may be mentioned, for example, a $C_1$ to $C_4$ alkyl group such as methyl, ethyl, propyl, isopropyl, butyl and isobutyl groups, etc., or an aralkyl group such as benzyl and phenylethyl groups, etc.; or a $C_2$ to $C_5$ alkanoyloxyalkyl group which is easily hydrolyzed in vivo to be converted into a carboxy group, such as acetoxymethyl and pivaloyloxymethyl groups, etc.; a $C_1$ to $C_4$ alkoxycarbonyloxyalkyl group such as 1-(ethoxycarbonyloxy)ethyl and 1-(isopropoxycarbonyloxy)ethyl groups, etc.; an N,N-dialkyl-substituted aminocarbonylalkyl group such as an N,N-dimethylaminocarbonylmethyl group, etc.; an N,N-dialkyl-substituted aminoalkyl group such as a 2-(N,N-dimethylamino)ethyl group, etc.; an alkyl group substituted by a 5-membered or 6-membered saturated heteromonocyclic ring containing 1 or 2 hetero atoms selected from N, O and S, such as 2-morpholinoethyl, 2-piperidinoethyl and 2-(4-methylpiperidino)ethyl groups, etc., or a (5-methyl-2-oxo-1,3-dioxolen-4-yl)methyl group or (5-phenyl-2-oxo-1,3-dioxolen-4-yl)methyl group.

In the present invention, the compound represented by the above formula (I) can be a pharmaceutically acceptable salt, if necessary.

As such a salt, there may be mentioned an acid addition salt of a mineral acid, such as hydrochloride, hydrobromide, hydroiodide, sulfate and phosphate, etc.; an acid addition salt of an organic acid, such as methanesulfonate, ethanesulfonate, benzenesulfonate, p-toluenesulfonate, oxalate, maleate, fumarate, tartrate and citrate, etc.; or a metal salt of a carboxylic acid, such as a sodium salt, a potassium salt, a calcium salt, a magnesium salt, a manganese salt, an iron salt and an aluminum salt, etc.

The compound (I) of the present invention can also exist as a hydrate.

Preferred compounds represented by the above formula (I) are illustrated in Table 1 to Table 10.

TABLE 1

| $R^2$ | $R^2$ |
|---|---|
| phenyl | 2-oxazolyl |
| 2-fluorophenyl | 2-thiazolyl |
| 3-fluorophenyl | 2-imidazolyl |

TABLE 1-continued

| $R^2$ | $R^2$ |
|---|---|
| 4-fluorophenyl | 2-pyridyl |
| 2-chlorophenyl | 6-methoxy-2-pyridyl |
| 3-chlorophenyl | 3-fluoro-2-pyridyl |
| 4-chlorophenyl | 3-pyridyl |
| 2-methoxyphenyl | 4-pyridyl |
| 3-methoxyphenyl | 2-benzoxazolyl |
| 4-methoxyphenyl | 5-chloro-2-benzoxazolyl |
| 2-ethoxyphenyl | 2-benzothiazolyl |
| 2-trifluoromethylphenyl | 5-methyl-2-benzothiazolyl |
| 3-trifluoromethylphenyl | 2-benzoimidazolyl |
| 4-trifluoromethylphenyl | 2-pyrimidinyl |
| 2,4-difluorophenyl | 5-chloro-2-pyrimidinyl |
| 2-methylphenyl | 4-methoxy-2-pyrimidinyl |
| 3-methylphenyl | 4,6-dimethoxy-2-pyrimidinyl |
| 2-methylthiophenyl | 4-pyrimidinyl |
| 3-methylthiophenyl | 6-ethyl-4-pyrimidinyl |
| 4-methylthiophenyl | 6-chloro-4-pyrimidinyl |
| 2-ethylthiophenyl | 5-chloro-6-methyl-4-pyrimidinyl |
| 3-ethylthiophenyl | 3-pyridazinyl |
| 4-ethylthiophenyl | 6-chloro-3-pyridazinyl |
| | 2-pyrazinyl |

TABLE 2

| $R^2$ | $R^2$ |
|---|---|
| phenyl | 2-oxazolyl |
| 2-fluorophenyl | 2-thiazolyl |
| 3-fluorophenyl | 2-imidazolyl |
| 4-fluorophenyl | 2-pyridyl |
| 2-chlorophenyl | 6-methoxy-2-pyridyl |
| 3-chlorophenyl | 3-fluoro-2-pyridyl |
| 4-chlorophenyl | 3-pyridyl |
| 2-methoxyphenyl | 4-pyridyl |
| 3-methoxyphenyl | 2-benzoxazolyl |
| 4-methoxyphenyl | 5-chloro-2-benzoxazolyl |
| 2-ethoxyphenyl | 2-benzothiazolyl |
| 2-trifluoromethylphenyl | 5-methyl-2-benzothiazolyl |
| 3-trifluoromethylphenyl | 2-benzoimidazolyl |
| 4-trifluoromethylphenyl | 2-pyrimidinyl |
| 2,4-difluorophenyl | 5-chloro-2-pyrimidinyl |
| 2-methylphenyl | 4-methoxy-2-pyrimidinyl |
| 3-methylphenyl | 4,6-dimethoxy-2-pyrimidinyl |
| 2-methylthiophenyl | 4-pyrimidinyl |
| 3-methylthiophenyl | 6-ethyl-4-pyrimidinyl |
| 4-methylthiophenyl | 6-chloro-4-pyrimidinyl |
| 2-ethylthiophenyl | 5-chloro-6-methyl-4-pyrimidinyl |
| 3-ethylthiophenyl | 3-pyridazinyl |
| 4-ethylthiophenyl | 6-chloro-3-pyridazinyl |
| | 2-pyrazinyl |

TABLE 3

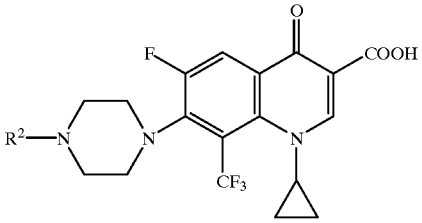

| R² | R² |
|---|---|
| phenyl | 2-oxazolyl |
| 2-fluorophenyl | 2-thiazolyl |
| 3-fluorophenyl | 2-imidazolyl |
| 4-fluorophenyl | 2-pyridyl |
| 2-chlorophenyl | 6-methoxy-2-pyridyl |
| 3-chlorophenyl | 3-fluoro-2-pyridyl |
| 4-chlorophenyl | 3-pyridyl |
| 2-methoxyphenyl | 4-pyridyl |
| 3-methoxyphenyl | 2-benzoxazolyl |
| 4-methoxyphenyl | 5-chloro-2-benzoxazolyl |
| 2-ethoxyphenyl | 2-benzothiazolyl |
| 2-trifluoromethylphenyl | 5-methyl-2-benzothiazolyl |
| 3-trifluoromethylphenyl | 2-benzoimidazolyl |
| 4-trifluoromethylphenyl | 2-pyrimidinyl |
| 2,4-difluorophenyl | 5-chloro-2-pyrimidinyl |
| 2-methylphenyl | 4-methoxy-2-pyrimidinyl |
| 3-methylphenyl | 4,6-dimethoxy-2-pyrimidinyl |
| 2-methylthiophenyl | 4-pyrimidinyl |
| 3-methylthiophenyl | 6-ethyl-4-pyrimidinyl |
| 4-methylthiophenyl | 6-chloro-4-pyrimidinyl |
| 2-ethylthiophenyl | 5-chloro-6-methyl-4-pyrimidinyl |
| 3-ethylthiophenyl | 3-pyridazinyl |
| 4-ethylthiophenyl | 6-chloro-3-pyridazinyl |
|  | 2-pyrazinyl |

TABLE 4

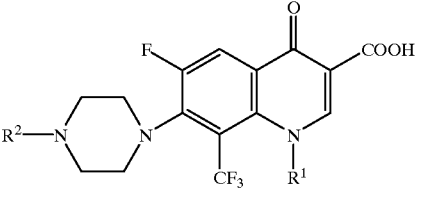

| R¹ | R² | R¹ | R² |
|---|---|---|---|
| propyl | phenyl | isopropyl | phenyl |
| " | 2-chlorophenyl | " | 2-chlorophenyl |
| " | 3-chlorophenyl | " | 3-chlorophenyl |
| " | 4-chlorophenyl | " | 4-chlorophenyl |
| " | 2-fluorophenyl | " | 2-fluorophenyl |
| " | 3-fluorophenyl | " | 3-fluorophenyl |
| " | 4-fluorophenyl | " | 4-fluorophenyl |
| " | 2-methoxyphenyl | " | 2-methoxyphenyl |
| " | 3-methoxyphenyl | " | 3-methoxyphenyl |
| " | 4-methoxyphenyl | " | 4-methoxyphenyl |
| " | 2-trifluoromethylphenyl | " | 2-trifluoromethylphenyl |
| " | 3-trifluoromethylphenyl | " | 3-trifluoromethylphenyl |
| " | 4-trifluoromethylphenyl | " | 4-trifluoromethylphenyl |
| " | 2-pyridyl | " | 2-pyridyl |
| " | 3-pyridyl | " | 3-pyridyl |
| " | 4-pyridyl | " | 4-pyridyl |
| " | 2-pyrimidinyl | " | 2-pyrimidinyl |
| " | 4-pyrimidinyl | " | 4-pyrimidinyl |
| " | 2-methylthiophenyl | " | 2-methylthiophenyl |
| " | 3-methylthiophenyl | " | 3-methylthiophenyl |
| " | 4-methylthiophenyl | " | 4-methylthiophenyl |
| " | 2-ethylthiophenyl | " | 2-ethylthiophenyl |

TABLE 4-continued

| R¹ | R² | R¹ | R² |
|---|---|---|---|
| " | 3-ethylthiophenyl | " | 3-ethylthiophenyl |
| " | 4-ethylthiophenyl | " | 4-ethylthiophenyl |

TABLE 5

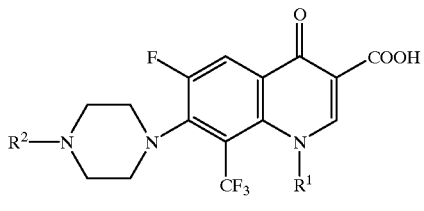

| R¹ | R² | R¹ | R² |
|---|---|---|---|
| butyl | phenyl | isobutyl | phenyl |
| " | 2-chlorophenyl | " | 2-chlorophenyl |
| " | 3-chlorophenyl | " | 3-chlorophenyl |
| " | 4-chlorophenyl | " | 4-chlorophenyl |
| " | 2-fluorophenyl | " | 2-fluorophenyl |
| " | 3-fluorophenyl | " | 3-fluorophenyl |
| " | 4-fluorophenyl | " | 4-fluorophenyl |
| " | 2-methoxyphenyl | " | 2-methoxyphenyl |
| " | 3-methoxyphenyl | " | 3-methoxyphenyl |
| " | 4-methoxyphenyl | " | 4-methoxyphenyl |
| " | 2-trifluoromethylphenyl | " | 2-trifluoromethylphenyl |
| " | 3-trifluoromethylphenyl | " | 3-trifluoromethylphenyl |
| " | 4-trifluoromethylphenyl | " | 4-trifluoromethylphenyl |
| " | 2-pyridyl | " | 2-pyridyl |
| " | 3-pyridyl | " | 3-pyridyl |
| " | 4-pyridyl | " | 4-pyridyl |
| " | 2-pyrimidinyl | " | 2-pyrimidinyl |
| " | 4-pyrimidinyl | " | 4-pyrimidinyl |
| " | 2-methylthiophenyl | " | 2-methylthiophenyl |
| " | 3-methylthiophenyl | " | 3-methylthiophenyl |
| " | 4-methylthiophenyl | " | 4-methylthiophenyl |
| " | 2-ethylthiophenyl | " | 2-ethylthiophenyl |
| " | 3-ethylthiophenyl | " | 3-ethylthiophenyl |
| " | 4-ethylthiophenyl | " | 4-ethylthiophenyl |

TABLE 6

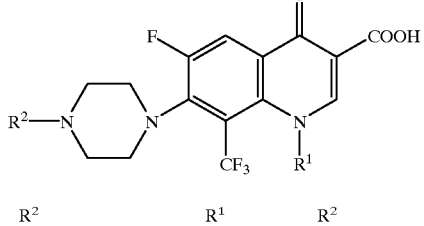

| R¹ | R² | R¹ | R² |
|---|---|---|---|
| t-butyl | phenyl | cyclobutyl | phenyl |
| " | 2-chlorophenyl | " | 2-chlorophenyl |
| " | 3-chlorophenyl | " | 3-chlorophenyl |
| " | 4-chlorophenyl | " | 4-chlorophenyl |

TABLE 6-continued

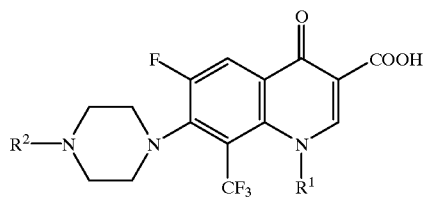

| R$^1$ | R$^2$ | R$^1$ | R$^2$ |
|---|---|---|---|
| " | 2-fluorophenyl | " | 2-fluorophenyl |
| " | 3-fluorophenyl | " | 3-fluorophenyl |
| " | 4-fluorophenyl | " | 4-fluorophenyl |
| " | 2-methoxyphenyl | " | 2-methoxyphenyl |
| " | 3-methoxyphenyl | " | 3-methoxyphenyl |
| " | 4-methoxyphenyl | " | 4-methoxyphenyl |
| " | 2-pyridyl | " | 2-pyridyl |
| " | 3-pyridyl | " | 3-pyridyl |
| " | 4-pyridyl | " | 4-pyridyl |
| " | 2-pyrimidinyl | " | 2-pyrimidinyl |
| " | 4-pyrimidinyl | " | 4-pyrimidinyl |
| " | 2-methylthiophenyl | " | 2-methylthiophenyl |
| " | 3-methylthiophenyl | " | 3-methylthiophenyl |
| " | 4-methylthiophenyl | " | 4-methylthiophenyl |
| " | 2-ethylthiophenyl | " | 2-ethylthiophenyl |
| " | 3-ethylthiophenyl | " | 3-ethylthiophenyl |
| " | 4-ethylthiophenyl | " | 4-ethylthiophenyl |

TABLE 7

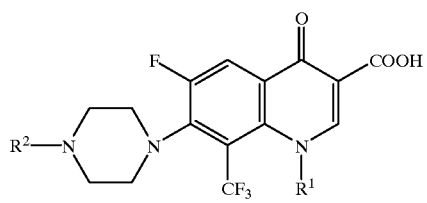

| R$^1$ | R$^2$ | R$^1$ | R$^2$ |
|---|---|---|---|
| cyclopentyl | phenyl | cyclohexyl | phenyl |
| " | 2-chlorophenyl | " | 2-chlorophenyl |
| " | 3-chlorophenyl | " | 3-chlorophenyl |
| " | 4-chlorophenyl | " | 4-chlorophenyl |
| " | 2-fluorophenyl | " | 2-fluorophenyl |
| " | 3-fluorophenyl | " | 3-fluorophenyl |
| " | 4-fluorophenyl | " | 4-fluorophenyl |
| " | 2-methoxyphenyl | " | 2-methoxyphenyl |
| " | 3-methoxyphenyl | " | 3-methoxyphenyl |
| " | 4-methoxyphenyl | " | 4-methoxyphenyl |
| " | 2-pyridyl | " | 2-pyridyl |
| " | 3-pyridyl | " | 3-pyridyl |
| " | 4-pyridyl | " | 4-pyridyl |
| " | 2-pyrimidinyl | " | 2-pyrimidinyl |
| " | 4-pyrimidinyl | " | 4-pyrimidinyl |
| " | 2-methylthiophenyl | " | 2-methylthiophenyl |
| " | 3-methylthiophenyl | " | 3-methylthiophenyl |
| " | 4-methylthiophenyl | " | 4-methylthiophenyl |
| " | 2-ethylthiophenyl | " | 2-ethylthiophenyl |
| " | 3-ethylthiophenyl | " | 3-ethylthiophenyl |
| " | 4-ethylthiophenyl | " | 4-ethylthiophenyl |

TABLE 8

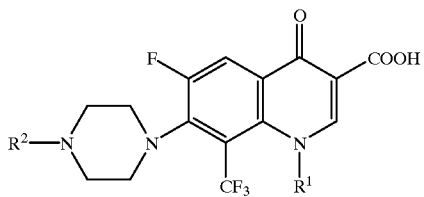

| R$^1$ | R$^2$ | R$^1$ | R$^2$ |
|---|---|---|---|
| 2-fluoroethyl | phenyl | 2-chloroethyl | phenyl |
| " | 2-chlorophenyl | 2,2,2-trifluoroethyl | " |
| " | 3-chlorophenyl | 2-chloroethyl | 2-chlorophenyl |
| " | 4-chlorophenyl | 2,2,2-trifluoroethyl | " |
| " | 2-fluorophenyl | 2-chloroethyl | 4-fluorophenyl |
| " | 3-fluorophenyl | 2,2,2-trifluoroethyl | " |
| " | 4-fluorophenyl | 2-chloroethyl | 2-methoxyphenyl |
| " | 2-methoxyphenyl | 2,2,2-trifluoroethyl | " |
| " | 3-methoxyphenyl | 2-chloroethyl | 2-pyridyl |
| " | 4-methoxyphenyl | 2,2,2-trifluoroethyl | " |
| " | 2-trifluoro-methylphenyl | 2-chloroethyl | 2-pyrimidinyl |
| " | 3-trifluoro-methylphenyl | 2,2,2-trifluoroethyl | " |
| " | 4-trifluoro-methylphenyl | | |
| " | 2-pyridyl | | |
| " | 3-pyridyl | | |
| " | 4-pyridyl | | |
| " | 2-pyrimidinyl | | |
| " | 4-pyrimidinyl | | |
| " | 2-methylthio-phenyl | | |
| " | 3-methylthio-phenyl | | |
| " | 4-methylthio-phenyl | | |
| " | 2-ethylthio-phenyl | | |
| " | 3-ethylthio-phenyl | | |
| " | 4-ethylthio-phenyl | | |

TABLE 9

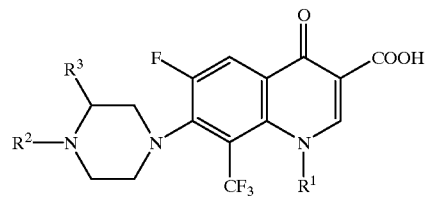

| R$^1$ | R$^2$ | R$^3$ |
|---|---|---|
| methyl | 2-pyridyl | methyl |
| " | 2-pyrimidinyl | " |
| " | 2-methoxyphenyl | " |
| " | 2-chlorophenyl | " |
| ethyl | 2-pyridyl | " |
| " | 2-pyrimidinyl | " |
| " | 2-methoxyphenyl | " |
| " | 2-chlorophenyl | " |
| isopropyl | 2-pyridyl | " |
| " | 2-pyrimidinyl | " |
| " | 2-methoxyphenyl | " |
| " | 2-chlorophenyl | " |
| cyclopropyl | 2-pyridyl | " |
| " | 2-pyrimidinyl | " |
| " | 2-methoxyphenyl | " |

TABLE 9-continued

[Structure: quinoline core with F at 6-position, CF3 at 8-position, COOH at 3-position, N-R1 at 1-position, and piperazine with R2 on far N and R3 substituent attached to 7-position]

| R¹ | R² | R³ |
|---|---|---|
| " | 2-chlorophenyl | " |
| 2-fluoroethyl | 2-pyridyl | " |
| " | 2-pyrimidinyl | " |
| " | 2-methoxyphenyl | " |
| " | 2-chlorophenyl | " |

TABLE 10

[Structure: quinoline core with F at 6-position, CF3 at 8-position, COOH at 3-position, N-R1 at 1-position, and piperidine with R2-N attached to 7-position]

| R¹ | R² |
|---|---|
| methyl | 2-pyridyl |
| " | 2-pyrimidinyl |
| " | 2-methoxyphenyl |
| " | 2-chlorophenyl |
| ethyl | 2-pyridyl |
| " | 2-pyrimidinyl |
| " | 2-methoxyphenyl |
| " | 2-chlorophenyl |
| isopropyl | 2-pyridyl |
| " | 2-pyrimidinyl |
| " | 2-methoxyphenyl |
| " | 2-chlorophenyl |
| cyclopropyl | 2-pyridyl |
| " | 2-pyrimidinyl |
| " | 2-methoxyphenyl |
| " | 2-chlorophenyl |
| 2-fluoroethyl | 2-pyridyl |
| " | 2-pyrimidinyl |
| " | 2-methoxyphenyl |
| " | 2-chlorophenyl |

As a more preferred compound represented by the formula (I), there may be mentioned 1-cyclopropyl-6-fluoro-8-trifluoromethyl-1,4-dihydro-4-oxo-7-[4-(2-pyrimidinyl)piperazin-1-yl]quinoline-3-carboxylic acid, 1-cyclopropyl-6-fluoro-8-trifluoromethyl-1,4-dihydro-4-oxo-7-[4-(2-pyridyl)piperazin-1-yl]quinoline-3-carboxylic acid, 1-cyclopropyl-6-fluoro-8-trifluoromethyl-1,4-dihydro-4-oxo-7-[4-(2-methoxyphenyl)piperazin-1-yl]quinoline-3-carboxylic acid, 1-cyclopropyl-6-fluoro-8-trifluoromethyl-1,4-dihydro-4-oxo-7-(4-phenylpiperazin-1-yl)quinoline-3-carboxylic acid, 1-cyclopropyl-6-fluoro-8-trifluoromethyl-1,4-dihydro-4-oxo-7-[4-(3-chlorophenyl)piperazin-1-yl]quinoline-3-carboxylic acid, 1-cyclopropyl-6-fluoro-8-trifluoromethyl-1,4-dihydro-4-oxo-7-[4-(4-fluorophenyl)piperazin-1-yl]quinoline-3-carboxylic acid, 1-cyclopropyl-6-fluoro-8-trifluoromethyl-1,4-dihydro-4-oxo-7-[4-(3-trifluoromethylphenyl)piperazin-1-yl]quinoline-3-carboxylic acid, 6-fluoro-8-trifluoromethyl-1,4-dihydro-4-oxo-1-methyl-7-[4-(2-pyrimidinyl)piperazin-1-yl]quinoline-3-carboxylic acid, 6-fluoro-8-trifluoromethyl-1,4-dihydro-4-oxo-1-methyl-7-[4-(2-pyridyl)piperazin-1-yl]quinoline-3-carboxylic acid, 1-ethyl-6-fluoro-8-trifluoromethyl-1,4-dihydro-4-oxo-7-[4-(2-pyrimidinyl)piperazin-1-yl]quinoline-3-carboxylic acid, 1-ethyl-6-fluoro-8-trifluoromethyl-1,4-dihydro-4-oxo-7-[4-(2-pyridyl)piperazin-1-yl]quinoline-3-carboxylic acid, 1-ethyl-6-fluoro-8-trifluoromethyl-1,4-dihydro-4-oxo-7-[4-(2-methoxyphenyl)piperazin-1-yl]quinoline-3-carboxylic acid, 6-fluoro-8-trifluoromethyl-1,4-dihydro-4-oxo-1-isopropyl-7-[4-(2-pyrimidinyl)piperazin-1-yl]quinoline-3-carboxylic acid, 6-fluoro-8-trifluoromethyl-1,4-dihydro-4-oxo-1-isopropyl-7-[4-(2-pyridyl)piperazin-1-yl]quinoline-3-carboxylic acid, 6-fluoro-8-trifluoromethyl-1,4-dihydro-4-oxo-1-isopropyl-7-[4-(2-methoxyphenyl)piperazin-1-yl]quinoline-3-carboxylic acid, 6-fluoro-1-(2-fluoroethyl)-8-trifluoromethyl-1,4-dihydro-4-oxo-7-[4-(2-pyrimidinyl)piperazin-1-yl]quinoline-3-carboxylic acid, 6-fluoro-1-(2-fluoroethyl)-8-trifluoromethyl-1,4-dihydro-4-oxo-7-[4-(2-pyridyl)piperazin-1-yl]quinoline-3-carboxylic acid, 6-fluoro-1-(2-fluoroethyl)-8-trifluoromethyl-1,4-dihydro-4-oxo-7-[4-(2-methoxyphenyl)piperazin-1-yl]quinoline-3-carboxylic acid, 6-fluoro-8-trifluoromethyl-1,4-dihydro-4-oxo-1-methyl-7-[4-(2-methoxyphenyl)piperazin-1-yl]quinoline-3-carboxylic acid, 6-fluoro-8-trifluoromethyl-1,4-dihydro-4-oxo-1-methyl-7-[4-(2-chlorophenyl)piperazin-1-yl]quinoline-3-carboxylic acid, 6-fluoro-8-trifluoromethyl-1,4-dihydro-4-oxo-1-methyl-7-(4-phenylpiperazin-1-yl)quinoline-3-carboxylic acid, 6-fluoro-8-trifluoromethyl-1,4-dihydro-4-oxo-1-methyl-7-[4-(4-fluorophenyl)piperazin-1-yl]quinoline-3-carboxylic acid, 6-fluoro-8-trifluoromethyl-1,4-dihydro-4-oxo-1-methyl-7-[4-(2-thiazolyl)piperazin-1-yl]quinoline-3-carboxylic acid, 6-fluoro-8-trifluoromethyl-1,4-dihydro-4-oxo-1-methyl-7-[4-(2-methylthiophenyl)piperazin-1-yl]quinoline-3-carboxylic acid, 1-ethyl-6-fluoro-8-trifluoromethyl-1,4-dihydro-4-oxo-7-[4-(4-methoxyphenyl)piperazin-1-yl]quinoline-3-carboxylic acid, 1-ethyl-6-fluoro-8-trifluoromethyl-1,4-dihydro-4-oxo-7-[4-(4-chlorophenyl)piperazin-1-yl]quinoline-3-carboxylic acid, 1-ethyl-6-fluoro-8-trifluoromethyl-1,4-dihydro-4-oxo-7-[4-(4-chloro-2-pyridyl)piperazin-1-yl]quinoline-3-carboxylic acid, 1-ethyl-6-fluoro-8-trifluoromethyl-1,4-dihydro-4-oxo-7-[4-(2-fluorophenyl)piperazin-1-yl]quinoline-3-carboxylic acid, 1-ethyl-6-fluoro-8-trifluoromethyl-1,4-dihydro-4-oxo-7-[4-(3-methoxyphenyl)piperazin-1-yl]quinoline-3-carboxylic acid, 1-cyclopropyl-6-fluoro-8-trifluoromethyl-1,4-dihydro-4-oxo-7-[4-(2-pyridyl)piperazin-1-yl]quinoline-3-carboxylic acid 2-morpholinoethyl ester, 6-fluoro-8-trifluoromethyl-1,4-dihydro-4-oxo-1-methyl-7-[3-methyl-4-(2-pyrimidinyl)piperazin-1-yl]quinoline-3-carboxylic acid, and
6-fluoro-8-trifluoromethyl-1,4-dihydro-4-oxo-1-methyl-7-[4-(2-pyrimidinyl)homopiperazin-1-yl]quinoline-3-carboxylic acid, as a further preferred compound, there may be mentioned
1-cyclopropyl-6-fluoro-8-trifluoromethyl-1,4-dihydro-4-oxo-7-[4-(2-pyridyl)piperazin-1-yl]quinoline-3-carboxylic acid,
6-fluoro-8-trifluoromethyl-1,4-dihydro-4-oxo-1-methyl-7-[4-(2-pyrimidinyl)piperazin-1-yl]quinoline-3-carboxylic acid,
6-fluoro-8-trifluoromethyl-1,4-dihydro-4-oxo-1-methyl-7-[4-(2-pyridyl)piperazin-1-yl]quinoline-3-carboxylic acid,
1-ethyl-6-fluoro-8-trifluoromethyl-1,4-dihydro-4-oxo-7-[4-(2-pyridyl)piperazin-1-yl]quinoline-3-carboxylic acid,
6-fluoro-8-trifluoromethyl-1,4-dihydro-4-oxo-1-methyl-7-[4-(4-fluorophenyl)piperazin-1-yl]quinoline-3-carboxylic acid, and
6-fluoro-8-trifluoromethyl-1,4-dihydro-4-oxo-1-methyl-7-[4-(2-thiazolyl)piperazin-1-yl]quinoline-3-carboxylic acid, and as a particularly preferred compound, there may be mentioned
1-cyclopropyl-6-fluoro-8-trifluoromethyl-1,4-dihydro-4-oxo-7-[4-(2-pyridyl)piperazin-1-yl]quinoline-3-carboxylic acid,
6-fluoro-8-trifluoromethyl-1,4-dihydro-4-oxo-1-methyl-7-[4-(2-pyrimidinyl)piperazin-1-yl]quinoline-3-carboxylic acid, and
6-fluoro-8-trifluoromethyl-1,4-dihydro-4-oxo-1-methyl-7-[4-(2-pyridyl)piperazin-1-yl]quinoline-3-carboxylic acid.

The compound represented by the above formula (I) is prepared by Method A or Method B shown below.

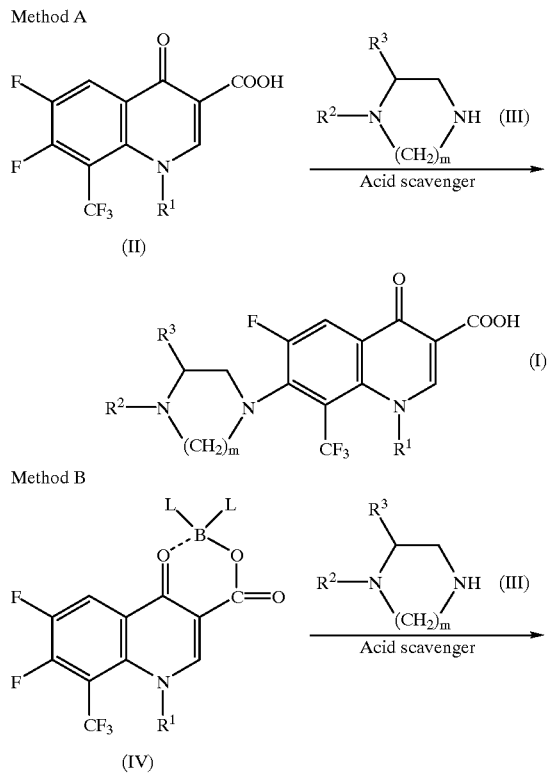

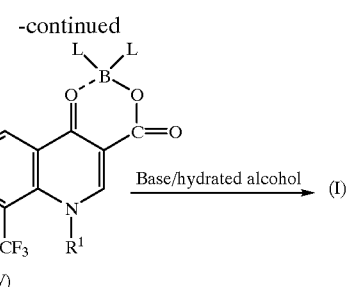

(wherein $R^1$, $R^2$, $R^3$ and m have the same meanings as defined above, and L represents a fluorine atom or an acetoxy group.)

In Method A, the desired compound (I) is prepared by coupling the quinolinecarboxylic acid compound (II) with the cyclic diamine (III) in the presence or absence of an acid scavenger and in the presence or absence of a solvent As the solvent to be used in this reaction, preferred is an aprotic polar solvent such as dimethyl sulfoxide, N,N-dimethylformamide, hexamethyliphosphoric triamide and N,N-dimethylacetamide, etc., and in addition, there may be used ketones such as acetone, methyl ethyl ketone, etc.; ethers such as diethyl ether, tetrahydrofuran, dioxane, etc.; esters such as ethyl acetate, etc.; alcohols such as methanol, ethanol, propanol, isopropanol, butanol, etc.; and nitrites such as acetonitrile, etc. As the acid scavenger, there may be used tertiary amines such as 1,8-diazabicyclo[5.4.0]-7-undecene, 1,5-diazabicyclo[4.3.0]-5-nonene, triethylamine, tributylamine, pyridine, picoline, lutidine and collidine, etc.; a metal alkoxide such as sodium methoxide, sodium ethoxide and potassium-t-butoxide, etc.; or an inorganic base such as sodium carbonate and potassium carbonate, etc.

The amount of the acid scavenger to be used is preferably an equimolar amount to 5-fold moles based on the compound (II), but in the case of the above tertiary amines, they may be used extremely excessively as a solvent. The excess cyclic diamine (III) also acts as an acid scavenger so that the reaction proceeds smoothly even when other acid scavenger is not added. The reaction is carried out at a temperature range of 0° C. to 200° C. generally for 0.5 hour to 24 hours.

In Method B, the desired compound (I) is prepared by coupling the boron chelate compound (IV) of carboxyquinolines with the cyclic diamine (III) in the presence or absence of an acid scavenger and in the presence or absence of a solvent in the same manner as in Method A to obtain the compound (V), and then reacting this compound in a hydrated alcohol in the presence of a base to decompose the chelate. The coupling reaction in Method B is carried out under the same conditions as described in the above Method A.

As the base to be used for decomposing the chelate in the above Method B, there may be mentioned an alkali hydroxide such as sodium hydroxide and potassium hydroxide, etc.; an alkali carbonate such as sodium carbonate and potassium carbonate, etc.; tertiary amines such as 1,8-diazabicyclo-[5.4.0]-7-undecene, 1,5-diazabicyclo[4.3.0]-5-nonene, triethylamine and 4-dimethylaminopyridine, etc.; or a metal alkoxide such as sodium methoxide, sodium ethoxide and potassium-t-butoxide, etc.

The amount of the base to be used is preferably an equimolar amount to 5-fold moles based on the compound (V), but an extremely excessive amount may be also used.

As the hydrated alcohol to be used as a solvent, there may be used, for example, methanol, ethanol, propanol, isopropanol and/or butanol, etc. containing 5 to 90% by weight of water.

The reaction is carried out at a range of 0° C. to 150° C. for 0.5 hour to 24 hours.

In the reactions described above, after completion of the reactions, the desired compounds of these reactions can be obtained by treating the reaction mixtures according to a conventional method, and, if necessary, they can be purified by a conventional purification means such as a recrystallization method, column chromatography, etc.

The compounds (I) thus obtained are made into desired salts according to a conventional method, if necessary.

The compound (I') in which the substituent $R^2$ of the above formula (I) is an aromatic heterocyclic ring group is also prepared by Method C shown below.

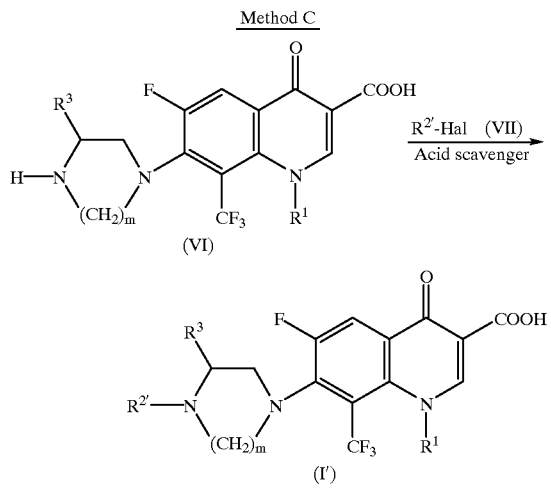

(wherein $R^1$ and $R^3$ have the same meanings as defined above, $R^2$ is an aromatic heterocyclic ring group, and Hal represents a halogen atom.)

The reaction of Method C is carried out in the same manner as described about Method A.

That is, the compound (I') is prepared by coupling the quinolinecarboxylic acid compound (VI) with an equimolar amount to 5-fold moles of the compound (VII) in the presence of an acid scavenger and in the presence or absence of a solvent.

As the solvent to be used in Method C, preferred is an aprotic polar solvent such as dimethyl sulfoxide, N,N-dimethylformamide, hexamethylphosphoric triamide and N,N-dimethylacetamide, etc., and in addition, there may be used ketones such as acetone, methyl ethyl ketone, etc.; ethers such as diethyl ether, tetrahydrofuran, dioxane, etc.; esters such as ethyl acetate, etc.; alcohols such as methanol, ethanol, propanol, isopropanol and butanol, etc.; nitrites such as acetonitrile, etc., and others.

As the acid scavenger, there may be used tertiary amines such as 1,8-diazabicyclo[5.4.0]-7-undecene, 1,5-diazabicyclo[4.3.0]-5-nonene, triethylamine, tributylamine, pyridine, picoline, lutidine and collidine, etc.; or an inorganic base such as sodium carbonate and potassium carbonate, etc.

The amount of the acid scavenger to be used is preferably an equimolar amount to 10-fold moles based on the compound (VII), but in the case of using the above tertiary amines, they may be used extremely excessively as a solvent.

The reaction is carried out at a temperature range of 0° C. to 200° C. generally for 1 hour to 24 hours.

The compound (VI) to be used as a starting material in Method C is prepared by using the compound (II) or (IV) as a material, using the cyclic diamine (III) in which $R^2$ is a hydrogen atom and reacting them in the same manner as in Method A or Method B.

The compound (II) to be used as a raw substance in the above Method A is prepared by, for example, Method D using the compound (VII) obtained by the method described in Japanese Patent Application Publication No. 66180/1989 as a starting material (see, for example, Japanese Patent Application Publication No. 255183/1993).

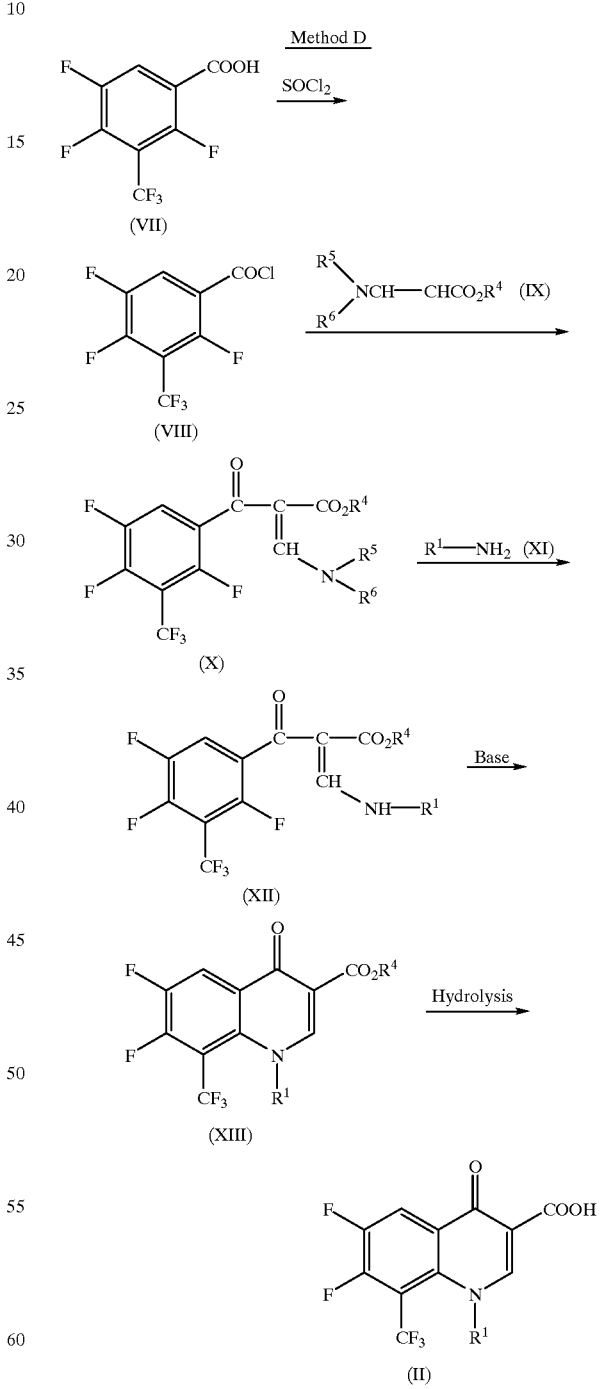

(wherein $R^1$ has the same meaning as defined above, $R^4$ represents a lower alkyl group, and $R^5$ and $R^6$ represent alkyl groups which are the same or different from each other.)

The boron chelate compound (IV) to be used as a raw substance in Method B is prepared easily from the compound (II) obtained by Method D or its lower alkyl ester compound (XIII) according to Method E (e.g., Japanese Patent Application Publication No. 198664/1988 (Reference example 8), Japanese Patent Application Publication No. 124873/1990 (Reference example 7) and Japanese Patent Application Publication No. 287577/1991 (Reference example 4)).

Method E

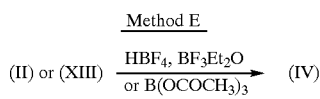

In the compounds represented by the above formula (I) prepared as described above, optical isomers may exist in some cases. In that case, optical isomers of the corresponding desired compounds (I) can be obtained by carrying out the above reaction using an optically resolved starting compound in a suitable stage. Also, the respective optical isomers can be also obtained by treating a mixture of optical isomers of the compounds represented by the formula (I) according to a conventional optical resolution method.

The carboxy group of the compound represented by the above formula (I) may be protected to form an ester as described above, and the ester-forming reaction is carried out from a corresponding carboxy compound and an alcohol according to a conventional method (e.g., a dehydration condensation method by an acid catalyst, a method through an acid halide, a dehydration condensation method by a carbodiimide, etc.).

The compound of the formula (I) is useful as an agent for treating AIDS by HIV. As an administration form for that purpose, there may be mentioned, for example, oral administration by a tablet, a capsule, a granule, a powder, a syrup, etc., or parenteral administration by an intravenous injection, an intramuscular injection, a suppository, etc. These agents are prepared by a known method, if necessary, by using additives such as an excipient, a binder, a disintegrating agent, a lubricant, a stabilizer, a flavor, etc. The dose varies depending on age, weight, disease conditions, administration form and administration times, etc., but the compound of the formula (I) is generally administered to an adult in a dose of about 10 to 500 mg per day, which is administered once or divided into several doses. When the compound of the formula (I) was orally administered to rats in a several-fold amount of the above dose (calculated based on weight), it did not exhibit toxicity.

Next, the present invention is explained more specifically by referring to Examples and Reference examples.

EXAMPLE 1

Synthesis of 1-cyclopropyl-6-fluoro-8-trifluoromethyl-1,4-dihydro-4-oxo-7-[4-(2-pyrimidinyl)piperazin-1-yl]quinoline-3-carboxylic acid In 20 ml of pyridine were dissolved 1.0 g (0.003 mole) of 1-cyclopropyl-6,7-difluoro-8-trifluoromethyl-1,4-dihydro-4-oxoquinoline-3-carboxylic acid and 1.23 g (0.0075 mole) of 1-(2-pyrimidinyl)piperazine, and the mixture was stirred at 105° C. for 3 hours. Then, the solvent was removed by evaporation under reduced pressure, and the residue was applied to silica gel column chromatography (eluent; a chloroform:methanol=9.5:0.5 mixed solution) to obtain 0.68 g of 1-cyclopropyl-6-fluoro-8-trifluoromethyl-1,4-dihydro-4-oxo-7-[4-(2-pyrimidinyl)piperazin-1-yl]quinoline-3-carboxylic acid as yellow powder.

Melting point: 285 to 287° C.

NMR (DMSO-$d_6$, $\delta$): 0.91 (2H, m), 1.17 to 1.18 (2H, m), 3.49 (4H, br.s), 3.94 (4H, br.s), 4.07 (1H, m), 6.69 to 6.71 (1H, t, J=9.3 Hz), 8.06 to 8.09 (1H, d, J=11.7 Hz), 8.42 to 8.43 (2H, d, J=4.4 Hz), 8.85 (1H, s), 14.58 (1H, s).

MS spectrum (CI): m/e 478 ($M^+$+1)

EXAMPLES 2 to 29

By the similar method as in Example 1, compounds of Table 11 were synthesized.

TABLE 11

| Example | $R^1$ | $R^2$ | $R^3$ | Property | Melting point (° C.) |
|---|---|---|---|---|---|
| 2 | cyclopropyl | 2-pyridyl | hydrogen atom | yellow powder | 225 to 226 |
| 3 | cyclopropyl | 2-methoxyphenyl | hydrogen atom | whitish pink powder | 196 to 197 |
| 4 | cyclopropyl | phenyl | hydrogen atom | slightly red powder | 245 to 247 |
| 5 | cyclopropyl | 3-chlorophenyl | hydrogen atom | ocher yellow powder | 235 to 237 |
| 6 | cyclopropyl | 4-fluorophenyl | hydrogen atom | light orange powder | 230.5 to 231.5 |
| 7 | cyclopropyl | 3-trifluoromethylphenyl | hydrogen atom | grayish white powder | 233 to 234 |
| 8 | methyl | 2-pyrimidinyl | hydrogen atom | pale yellow powder | 280 to 282 |
| 9 | " | 2-pyridyl | hydrogen atom | yellow powder | 264 to 266 |
| 10 | ethyl | 2-pyrimidinyl | hydrogen atom | yellow powder | 265.5 to 267 |
| 11 | " | 2-pyridyl | hydrogen atom | yellow powder | 259 to 260 |
| 12 | " | 2-methoxyphenyl | hydrogen atom | yellow-tinted white powder | 197 to 199 |
| 13 | isopropyl | 2-pyrimidinyl | hydrogen atom | yellow powder | 285 to 288 |
| 14 | isopropyl | 2-pyridyl | hydrogen atom | pale yellow powder | 266 to 268 |
| 15 | isopropyl | 2-methoxyphenyl | hydrogen atom | ocher yellow powder | 196 to 198 |
| 16 | 2-fluoroethyl | 2-pyrimidinyl | hydrogen atom | yellow powder | 271.5 to 273.5 |
| 17 | 2-fluoroethyl | 2-pyridyl | hydrogen atom | yellow powder | 246 to 248 |
| 18 | 2-fluoroethyl | 2-methoxyphenyl | hydrogen atom | yellow-tinted white powder | 225 to 226 |
| 19 | methyl | 2-methoxyphenyl | hydrogen atom | ocher yellow powder | 252 to 253 |
| 20 | " | 2-chlorophenyl | hydrogen atom | bright orange powder | 275 to 278 |
| 21 | " | phenyl | hydrogen | bright or- | 258.5 to |

TABLE 11-continued

| Example | R¹ | R² | R³ | Property | Melting point (° C.) |
|---|---|---|---|---|---|
| 22 | methyl | 4-fluorophenyl | hydrogen atom | bright orange powder | 269 to 270 |
| 23 | " | 2-thiazolyl | hydrogen atom | yellow powder | 266 to 267 |
| 24 | " | 2-methylthiophenyl | hydrogen atom | ocher yellow powder | 242 to 243 |
| 25 | ethyl | 4-methoxyphenyl | hydrogen atom | light red powder | 235 to 236 |
| 26 | " | 4-chlorophenyl | hydrogen atom | pink powder | 274 to 276 |
| 27 | " | 5-chloro-2-pyridyl | hydrogen atom | pale yellow powder | 283 to 285 |
| 28 | " | 2-fluorophenyl | hydrogen atom | ocher yellow powder | 228 to 230 |
| 29 | " | 3-methoxyphenyl | hydrogen atom | light red powder | 217.5 to 218.5 |

(row 22 continued from previous: orange powder 260.5)

EXAMPLE 30

Synthesis of 1-cyclopropyl-6-fluoro-8-trifluoromethyl-1,4-dihydro-4-oxo-7-[4-(2-pyridyl)-piperazin-1-yl]quinoline-3-carboxylic acid 2-morpholinoethyl ester To 5 ml of methylene chloride were added 100 mg (0.21 mmole) of 2-cyclopropyl-6-fluoro-8-trifluoromethyl-1,4-dihydro-4-oxo-7-[4-(2-pyridyl)piperazin-1-yl]quinoline-3-carboxylic acid, 0-055 g (0.42 mmole) of 4-(2-hydroxyethyl)morpholine, 0.045 g (0.37 mmole) of 4-dimethylaminopyridine and 0.091 g (0.48 mmole) of 1-ethyl-3-(3-dimethyaminopropyl)carbodiimide hydrochloride, the mixture was left to stand at room temperature for 7 days, and then the solvent was removed by evaporation under reduced pressure. The residue was applied to column chromatography (eluent; a chloroform:methanol:28% aqueous ammonia=40:9:1 mixed solution) to obtain 60 mg of 1-cyclopropyl-6-fluoro-8-trifluoromethyl-1,4-dihydro-4-oxo-7-[4-(2-pyridyl)piperazin-1-yl]quinoline-3-carboxylic acid 2-morpholinoethyl ester as pale yellow powder.

Melting point: 203 to 205° C.

MS spectrum (CI): m/e 590 (M$^+$+1)

EXAMPLE 31

Synthesis of 6-fluoro-8-trifluoromethyl-1,4-dihydro-4-oxo-1-methyl-7-[3-methyl-4-(2-pyrimidinyl)piperazin-1-yl]quinoline-3-carboxylic acid In 30 ml of pyridine were dissolved 1.5 g (0.0049 mole) of 6,7-difluoro-8-trifluoromethyl-1,4-dihydro-1-methyl-4-oxoquinoline-3-carboxylic acid and 1.5 g (0.015 mole) of 2-methylpiperazine, the mixture was stirred at 105° C. for 3 hours, and then the solvent was removed by evaporation under reduced pressure. Ethanol was added to the residue, precipitated crystals were collected by filtration, the crystals obtained were washed with ethanol and dried, and then 1.49 g of 6-fluoro-8-trifluoromethyl-1,4-dihydro-4-oxo-1-methyl-7-(3-methylpiperazin-1-yl)quinoline-3-carboxylic acid was obtained as yellow powder.

To 20 ml of N,N-dimethylformamide were added 1.49 g (0.0039 mole) of the obtained 6-fluoro-8-trifluoromethyl-1,4-dihydro-4-oxo-1-methyl-7-(3-methylpiperazin-1-yl)quinoline-3-carboxylic acid, 0.88 g (0.0077 mole) of 2-chloropyrimidine and 0.78 g (0.0077 mole) of triethylamine, the mixture was stirred at 130° C. for 10 hours, and then the solvent was removed by evaporation under reduced pressure.

The residue was applied to silica gel column chromatography (eluent; a chloroform:methanol=9:1 mixed solution) to obtain 0.35 g of 6-fluoro-8-trifluoromethyl-1,4-dihydro-4-oxo-1-methyl-7-[3-methyl-4-(2-pyrimidinyl)piperazin-1-yl]-quinoline-3-carboxylic acid as ocher yellow powder.

Melting point: 283 to 284.5° C.

MS spectrum (CI): m/e 466 (M$^+$+1)

Elemental analysis value (%); in terms of $C_{21}H_{19}F_4N_5O_3 \cdot \frac{1}{2}H_2O$. Theoretical value; C: 53.17, H: 4.25, N: 14.76. Found value; C: 53.47, H: 4.07, N: 14.95.

EXAMPLE 32

Synthesis of 6-fluoro-8-trifluoromethyl-1,4-dihydro-4-oxo-1-methyl-7-[4-(2-pyrimidinyl)homopiperazin-1-yl)quinoline-3-carboxylic acid In 12 ml of pyridine were dissolved 0.8 g (0.0026 mole) of 6,7-difluoro-8-trifluoromethyl-1,4-dihydro-1-methyl-4-oxoquinoline-3-carboxylic acid and 2.1 g (0.0118 mole) of 1-(2-pyrimidinyl)homopiperazine, the mixture was stirred at 105° C. for 3 hours, and then the solvent was removed by evaporation under reduced pressure. The residue was applied to silica gel column chromatography (eluent; a chloroform:methanol=9.5:0.5 mixed solution) to obtain 0.45 g of 6-fluoro-8-trifluoromethyl-1,4-dihydro-4-oxo-1-methyl-7-[4-(2-pyrimidinyl)homopiperazin-1-yl)quinoline-3-carboxylic acid as yellow powder.

Melting point: 243 to 245° C.

MS spectrum (CI): m/e 466 (M$^+$+1)

Elemental analysis value (%); in terms of $C_{21}H_{19}F_4N_5O_3$. Theoretical value; C: 54.20, H: 4.11, N: 15.05. Found value; C: 54.06, H: 4.03, N: 14.96.

EXAMPLE 33

Measurement of the anti-HIV activities of the compounds of the present invention was carried out according to the method of R. Pauwel et al. (J. Virological Method 20, p. 309 to 321 (1988)). That is, MT-4 cells were centrifuged (1000× g, 5 minutes), and a cell-floating solution in which the resulting cellular sediments were suspended in a RPMI-1640 medium containing no serum was inoculated with HIV. The mixture was cultured at 37° C. for 1 hour and then added to a RPMI-1640 medium to which 10% bovine fetal serum was added (hereinafter referred to as the serum medium), and the mixture was washed and centrifuged (1000×g, 5 minutes). The HIV-infected cells thus obtained and HIV-non-infected cells were suspended in the serum media in an amount of 4×10⁵/ml, respectively, and each 100 μl of the suspensions were apportioned to the respective wells of a multiwell with 96 wells for tissue culture. Each 100 μl of the compounds which had been previously diluted with the serum medium stepwisely were apportioned to these respective wells, and then the mixtures were left to stand and cultured at 37° C.

for 5 days in the presence of 5% carbon dioxide. In the same manner, the HIV-infected cells and the HIV-non-infected cells to which the compound was not added were cultured. After completion of the culture, living cells were measured by using MTT (4,5-dimethylthiazol-2-yl)-2,5-diphenyltetrazolium bromide) to determine a cellular disorder-suppressing activity (an anti-HIV activity) brought about by adding the compound. It was confirmed that no mycoplasma was contained in the cell solution and the virus-inoculated solution.

The cellular disorder-suppressing activity against the HIV-non-infected cells to which the compound was not added was defined as 100%, and the cellular disorder-suppressing activity against the HIV-infected cells to which the compound was not added was defined as 0%. A compound concentration ($EC_{50}$) at which 50% cellular disorder-suppressing activity against the HIV-infected cells was exhibited was determined. The test results are shown in Table 12.

TABLE 12

| Example compound | $EC_{50}$ (μg/ml) |
|---|---|
| 2 | 0.02 |
| 8 | 0.02 |
| 9 | 0.005 |
| 11 | 0.01 |
| 22 | 0.0096 |
| 23 | 0.011 |
| Compound of Example 67 of Japanese Provisional Patent Publication No. 116241/1994 | 0.2 |

REFERENCE EXAMPLE 1

Synthesis of 1-cyclopropyl-6,7-difluoro-8-trifluoromethyl-1,4-dihydro-4-oxoquinoline-3-carboxylic acid (II; $R^1$=cyclopropyl)

30 ml of benzene, 17 ml of thionyl chloride and several drops of N,N-dimethylformamide were added to 8.5 g (0.0348 mole) of 2,4,5-trifluoro-3-trifluoromethylbenzoic acid (VII), and the mixture was refluxed under heating for 3 hours. After the reaction, benzene and excess thionyl chloride were removed by evaporation under reduced pressure to obtain 2,4,5-trifluoro-3-trifluoromethylbenzoic acid chloride (VIII).

After 5.47 g (0.0383 mole) of ethyl 3-dimethylaminoacrylate (IX; $R^3$=ethyl, $R^4$=$R^5$=methyl) was dissolved in 30 ml of anhydrous tetrahydrofuran, 4.2 g (0.0415 mole) of triethylamine was added to the solution, and a solution in which the above acid chloride was dissolved in 7 ml of anhydrous tetrahydrofuran at room temperature was gradually added dropwise to the mixture. After completion of the dropwise addition, the resulting mixture was heated at 50° C. for 3 hours, cooled to room temperature and then filtered. To the filtrate was added 3.9 g (0.0417 mole) of cyclopropylamine (XI; $R^1$=cyclopropyl) hydrochloride, and the mixture was stirred at 40° C. for 30 minutes. The mixture was cooled to room temperature and then filtered, the filtrate was concentrated under reduced pressure, and the residue was applied to silica gel column chromatography (eluent; an ethyl acetate:toluene=1:4 mixed solution) to obtain 10.63 g of ethyl 2-(2,4,5-trifluoro-3-trifluoromethylbenzoyl)-3-cyclopropylaminoacrylate (XII; $R^1$=cyclopropyl, $R^3$=ethyl) as a pale yellow solid. This compound was dissolved in 100 ml of anhydrous diethyl ether, 1.6 g (0.0416 mole) of 62.4% sodium hydride-mineral oil was gradually added to the solution under ice cooling, and the mixture was stirred at room temperature for 1 hour. To the reaction mixture was added 41.7 ml of 1 N hydrochloric acid, the mixture was vigorously stirred to make the whole reaction mixture acidic, and precipitated crystals were collected by filtration, washed with water and then washed with diethyl ether to obtain 7.32 g of 1-cyclopropyl-6,7-difluoro-8-trifluoromethyl-1,4-dihydro-4-oxoquinoline-3-carboxylic acid ethyl ester (XIII; $R^1$=cyclopropyl, $R^3$=ethyl) as white powder.

Melting point: 184 to 185° C.

MS spectrum (CI): m/e 362 ($M^+$+1)

Then, 0.8 g (0.0022 mole) of this ester compound was suspended in a mixed solution of 5 ml of acetic acid, 3 ml of water and 0.3 ml of concentrated sulfuric acid, and under stirring, the mixture was refluxed under heating for 2 hours. After the mixture was cooled to room temperature, water was added thereto, insolubles were removed by filtration, and the residue collected by filtration was washed with water and then dried to obtain 0.7 g of 1-cyclopropyl-6,7-difluoro-8-trifluoromethyl-1,4-dihydro-4-oxoquinoline-3-carboxylic acid (II; $R^1$=cyclopropyl) as white crystals.

Melting point: 210 to 212° C.

MS spectrum (CI): m/e 334 ($M^+$+1)

REFERENCE EXAMPLE 2

Synthesis of 1-ethyl-6,7-difluoro-8-trifluoromethyl-1,4-dihydro-4-oxoquinoline-3-carboxylic acid (II; $R^1$=ethyl)

The similar reaction of Reference example 1 was carried out by using ethylamine (XI; $R^1$=ethyl) in place of cyclopropylamine hydrochloride to obtain 1-ethyl-6,7-difluoro-8-trifluoromethyl-1,4-dihydro-4-oxoquinoline-3-carboxylic acid (II; $R^1$=ethyl) as white powder.

Melting point: 159 to 162° C.

MS spectrum (CI): m/e 322 ($M^+$+1)

REFERENCE EXAMPLE 3

Synthesis of 6,7-difluoro-8-trifluoromethyl-1,4-dihydro-1-methyl-4-oxoquinoline-3-carboxylic acid (II; $R^1$=methyl)

The similar reaction of Reference example 1 was carried out by using methylamine hydrochloride (II; $R^1$=methyl) in place of cyclopropylamine hydrochloride to obtain 6,7-difluoro-8-trifluoromethyl-1,4-dihydro-1-methyl-4-oxoquinoline-3-carboxylic acid (II; $R^1$=methyl) as white powder.

Melting point: 197.5 to 199° C.

MS spectrum (CI): m/e 308 ($M^+$+1)

REFERENCE EXAMPLE 4

Synthesis of 6,7-difluoro-8-trifluoromethyl-1,4-dihydro-1-isopropyl-4-oxoquinoline-3-carboxylic acid (II; $R^1$=isopropyl)

The similar reaction of Reference example 1 was carried out by using isopropylamine hydrochloride (XI; $R^1$=isopropyl) in place of cyclopropylamine hydrochloride to obtain 6,7-difluoro-8-trifluoromethyl-1,4-dihydro-1-isopropyl-4-oxoquinoline-3-carboxylic acid (II; $R^1$=isopropyl) as white powder.

Melting point: 197.5 to 200° C.

MS spectrum (CI): m/e 336 (M⁺+1)

REFERENCE EXAMPLE 5

Synthesis of 6,7-difluoro-1-(2-fluoroethyl)-8-trifluoromethyl-1,4-dihydro-4-oxoquinoline-3-carboxylic acid (II; $R^1$=2-fluoroethyl)

The similar reaction of Reference example 1 was carried out by using 2-fluoroethylamine hydrochloride (XI; $R^1$=2-fluoroethyl) in place of cyclopropylamine hydrochloride to obtain 6,7-difluoro-1-(2-fluoroethyl)-8-trifluoromethyl-1,4-dihydro-4-oxoquinoline-3-carboxylic acid (II; $R^1$=2-fluoroethyl) as white powder.

Melting point: 183 to 185° C.

MS spectrum (CI): m/e 340 (M⁺+1)

REFERENCE EXAMPLE 6

Synthesis of 1-(2-pyrimidyl)homopiperazine 50 ml of acetonitrile was added to 10.0 g (0.1 mole) of homopiperazine, 2.9 g (0.025 mole) of 2-chloropyrimidine, 6.9 g (0.05 mole) of potassium carbonate and a catalytic amount of potassium iodide, and the mixture was refluxed under heating for 11 hours. The mixture was cooled to room temperature and then filtered, the filtrate obtained was concentrated under reduced pressure, and the residue was applied to silica gel column chromatography (eluent; a chloroform:methanol=8:2 mixed solution) to obtain 2.14 g of 1-(2-pyrimidyl)homopiperazine as a pale yellow liquid.

MS spectrum (CI): m/e 179 (M⁺+1)

REFERENCE EXAMPLE 7

Synthesis of 1-(2-methylthiophenyl)piperazine 40 ml of ethanol was added to 2.8 g (0.02 mole) of 2-methylthioaniline and 13.7 g (0.044 mole) of acid N-bis (2-bromoethyl)amine hydrobromide, and the mixture was refluxed under heating for 10 hours. After the mixture was cooled to room temperature, 10.2 g of potassium carbonate was added thereto, and the resulting mixture was refluxed under heating for 10 hours. After the mixture was cooled to room temperature and then filtered, the filtrate obtained was concentrated under reduced pressure, and the residue was applied to silica gel column chromatography (eluent; a chloroform:methanol:28% aqueous ammonia=40:9:1 mixed solution) to obtain 1.31 g of 1-(2-methylthiophenyl) piperazine as a pale yellow liquid.

MS spectrum (CI): m/e 209 (M⁺+1)

REFERENCE EXAMPLE 8

Synthesis of 1-(2-thiazolyl)-piperazine

In 50 ml of acetonitrile was dissolved 5.0 g (0.0305 mole) of 2-bromothiazole, then, 13.1 g (0.153 mole) of piperazine, 8.4 g (0.061 mole) of potassium carbonate and a catalytic amount of potassium iodide were added to the solution, and the mixture was refluxed under heating for 5 hours. After the mixture was cooled to room temperature and then filtered, the filtrate was concentrated under reduced pressure, and the residue was applied to silica gel column chromatography (eluent; a chloroform:methanol:28% aqueous ammonia= 40:9:1 mixed solution) to obtain 3.62 g of 1-(2-thiazolyl) piperazine as a colorless liquid.

MS spectrum (CI): m/e 170 (M⁺+1)

UTILIZABILITY IN INDUSTRY

According to the present invention, a novel 8-trifluoromethylquinolinecarboxylic acid derivative which specifically suppresses growth of HIV in HIV-infected cells and further has an activity of suppressing a cytopathic effect (CPE) by HIV, or a pharmaceutically acceptable salt thereof or an ester are provided.

We claim:

1. A 8-trifluoromethylquinolinecarboxylic acid compound represented by the following formula (I):

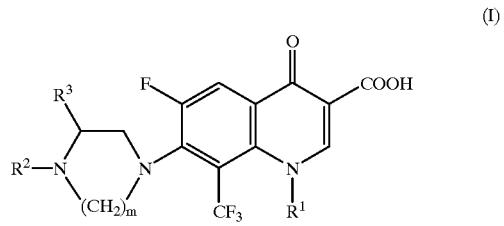

wherein
$R^1$ represents a $C_1$ to $C_4$ alkyl group, a halogeno-$C_1$ to $C_4$ alkyl group or a $C_3$ to $C_6$ cycloalkyl group,
$R^2$ represents a phenyl group which is unsubstituted or substituted by a substituent $R^0$, a 5-membered or 6-membered aromatic heteromonocyclic ring group containing 1 or 2 hetero atoms selected from the group consisting of N, O and S, which is unsubstituted or substituted by said $R^0$, or an aromatic heterocyclic fused ring group in which said heteromonocyclic ring group and a benzene ring are fused, which is unsubstituted or substituted by said $R^0$,
said $R^0$ represents a halogen, a $C_1$ to $C_4$ alkyl, a fluorine-substituted $C_1$ to $C_4$ alkyl, a $C_1$ to $C_4$ alkoxy or a $C_1$ to $C_4$ alkylthio,
$R^3$ represents hydrogen or a $C_1$ to $C_4$ alkyl group, and
m represents an integer of 2,
provided that a compound wherein $R^1$ is an ethyl group, $R^2$ is a trifluoromethyl group and $R^3$ is a 2-pyrimidiniyl group is excluded;
or a pharmaceutically acceptable salt or ester thereof.

2. The 8-trifluoromethylquinolinecarboxylic acid compound according to claim 1 or a pharmaceutically acceptable salt or ester thereof, wherein $R^1$ is selected from the group consisting of methyl, ethyl, propyl, isopropyl, butyl, isobutyl, s-butyl, t-butyl, fluoromethyl, chloromethyl, difluoromethyl, trifluoromethyl, 2-fluoroethyl, 2-chloroethyl, 2-bromoethyl, 2-iodoethyl, 2,2,2-trifluoroethyl, 3-fluoropropyl, 3-chloropropyl, 3-bromopropyl, 4-fluorobutyl, cyclopropyl, cyclobutyl, cyclopentyl and cyclohexyl groups.

3. The 8-trifluoromethylquinolinecarboxylic acid compound according to claim 1 or a pharmaceutically acceptable salt or ester thereof, wherein $R^1$ is selected from the group consisting of methyl, ethyl, propyl, isopropyl, 2-fluoroethyl, 2-chloroethyl, 2,2,2-trifluoroethyl, cyclopropyl, cyclobutyl and cyclopentyl groups.

4. The 8-trifluoromethylquinolinecarboxylic acid compound according to claim 1 or a pharmaceutically acceptable salt or ester thereof, wherein $R^1$ is selected from the group consisting of methyl, ethyl, 2-fluoroethyl and cyclopropyl groups.

5. The 8-trifluoromethylquinolinecarboxylic acid compound according to claim 1 or a pharmaceutically acceptable salt or ester thereof, wherein $R^2$ is a phenyl group.

6. The 8-trifluoromethylquinolinecarboxylic acid compound according to claim 1 or a pharmaceutically acceptable salt or ester thereof, wherein the substituent $R^0$ of $R^2$ is selected from the group consisting of fluorine, chlorine, bromine, iodine, methyl, ethyl, propyl, isopropyl, butyl, s-butyl, isobutyl, t-butyl, mono-, di- or trifluoromethyl, 2-fluoroethyl, 2- or 3-fluoropropyl, 2-, 3- or 4-fluorobutyl, methoxy, ethoxy, propoxy, isopropoxy, butoxy, isobutoxy, s-butoxy, t-butoxy, methylthio, ethylthio, propylthio, isopropylthio, butylthio, isobutylthio, s-butylthio and t-butylthio groups.

7. The 8-trifluoromethylquinolinecarboxylic acid compound according to claim 1 or a pharmaceutically acceptable salt or ester thereof, wherein the substituent $R^0$ of $R^2$ is selected from the group consisting of fluorine, chlorine, methyl, ethyl, trifluoromethyl, methoxy, ethoxy, methylthio and ethylthio groups.

8. The 8-trifluoromethylquinolinecarboxylic acid compound according to claim 1 or a pharmaceutically acceptable salt or ester thereof, wherein the substituent $R^0$ of $R^2$ is selected from the group consisting of fluorine, chlorine, ethyl, trifluoromethyl, methoxy and methylthio groups.

9. The 8-trifluoromethylquinolinecarboxylic acid compound according to claim 1 or a pharmaceutically acceptable salt or ester thereof, wherein the aromatic heteromonocyclic ring or aromatic heterocyclic fused ring group of $R^2$ is selected from the group consisting of 2-thienyl, 2-furyl, 2-oxazolyl, 2-thiazolyl, 2-imidazolyl, 2-, 3- or 4-pyridyl, 2-, 4- or 5-pyrimidinyl, 2-pirazinyl, 3-pyridazinyl, 2-benzoxazolyl, 2-benzothiazolyl and 2-benzoimidazolyl groups.

10. The 8-trifluoromethylquinolinecarboxylic acid compound according to claim 1 or a pharmaceutically acceptable salt or ester thereof, wherein the aromatic heteromonocyclic ring or aromatic heterocyclic fused ring group of $R^2$ is selected from the group consisting of 2-thienyl, 2-furyl, 2-oxazolyl, 2-thiazolyl, 2-imidazolyl, 2-, 3- or 4-pyridyl, 2-, 4- or 5-pyrimidinyl, 2-pirazinyl and 3-pyridazinyl groups.

11. The 8-trifluoromethylquinolinecarboxylic acid compound according to claim 1 or a pharmaceutically acceptable salt or ester thereof, wherein the aromatic heteromonocyclic ring or aromatic heterocyclic fused ring group of $R^2$ is a 2-pyridyl or 2-pyrimidinyl group.

12. The 8-trifluoromethylquinolinecarboxylic acid compound according to claim 1 or a pharmaceutically acceptable salt or ester thereof, wherein $R^3$ is a hydrogen atom.

13. The 8-trifluoromethylquinolinecarboxylic acid compound according to claim 1 or a pharmaceutically acceptable salt or ester thereof, wherein $R^3$ is a $C_1$ to $C_4$ alkyl group.

14. The 8-trifluoromethylquinolinecarboxylic acid compound according to claim 1 or a pharmaceutically acceptable salt or ester thereof, wherein $R^3$ is selected from the group consisting of methyl, ethyl, propyl and isopropyl groups.

15. The 8-trifluoromethylquinolinecarboxylic acid compound according to claim I or a pharmaceutically acceptable salt or ester thereof, wherein $R^3$ is a methyl or ethyl group.

16. The 8-trifluoromethylquinolinecarboxylic acid compound according to claim 1 or a pharmaceutically acceptable salt or ester thereof, wherein the carboxyl group of the formula (I) is an ester protected by a protective group selected from the group consisting of a $C_1$ to $C_4$ alkyl group, an aralkyl group, a $C_2$ to $C_5$ alkanoyloxyalkyl group, a $C_1$ to $C_4$ alkoxycarbonyloxyalkyl group, an N,N-dialkyl-substituted aminocarbonylalkyl group, an alkyl group substituted by a 5-membered or 6-membered saturated heteromonocyclic ring containing 1 or 2 hetero atoms selected from N, O and S, and a (5-methyl(or 5-phenyl)-2-oxo-1,3-dioxolen-4-yl)methyl group.

17. The 8-trifluoromethylquinolinecarboxylic acid compound according to claim 1 or a pharmaceutically acceptable salt or ester thereof, wherein the carboxyl group of the formula (I) is an ester protected by a protective group selected from the group consisting of methyl, ethyl, propyl, isopropyl, butyl and isobutyl, benzyl and phenylethyl, acetoxymethyl, pivaloyloxymethyl, 1-(ethoxycarbonyloxy) ethyl, 1-(isopropoxycarbonyloxy)ethyl, an N,N-dimethylaminocarbonylmethyl group, 2-(N,N-dimethylamino)ethyl; 2-morpholinoethyl-substituted alkyl, 2-piperidinoethyl-substituted alkyl, 2-(4-methylpiperidino) ethyl-substituted alkyl and (5-methyl(or 5-phenyl)-2-oxo-1, 3-dioxolen-4-yl)methyl groups.

18. The 8-trifluoromethylquinolinecarboxylic acid compound according to claim 1 or a pharmaceutically acceptable salt or ester thereof, wherein the compound of the formula (I) is an acid addition salt of a mineral acid, an acid addition salt of an organic acid or a metal salt of a carboxylic acid.

19. The 8-trifluoromethylquinolinecarboxylic acid compound according to claim 1 or a pharmaceutically acceptable salt or ester thereof, wherein the compound of the formula (I) is a salt selected from the group consisting of hydrochloride, hydrobromide, hydroiodide, sulfate, phosphate, methanesulfonate, ethanesulfonate, benzenesulfonate, p-toluenesulfonate, oxalate, maleate, fumarate, tartrate, citrate, a sodium salt, a potassium salt, a calcium salt, a magnesium salt, a manganese salt, an iron salt and an aluminum salt.

20. 1-Cyclopropyl-6-fluoro-8-trifluoromethyl-1,4-dihydro-4-oxo-7-[4-(2-pyridyl)piperazin-1-yl]quinoline-3-carboxylic acid or a pharmaceutically acceptable salt or ester thereof.

21. 6-Fluoro-8-trifluoromethyl-1,4-dihydro-4-oxo-1-methyl-7-[4-(2-pyrimidinyl)piperazin-1-yl]quinoline-3-carboxylic acid or a pharmaceutically acceptable salt or ester.

22. 6-Fluoro-8-trifluoromethyl-1,4-dihydro-4-oxo-1-methyl-7-[4-(2-pyridyl)piperazin-1-yl]quinoline-3-carboxylic acid or a pharmaceutically acceptable salt or ester thereof.

23. A medical composition for inhibiting growth of human immunodeficient virus which comprises at least one 8-trifluoromethylquinolinecarboxylic acid compound according to claim 1 or a pharmaceutically acceptable salt thereof or a pharmaceutically acceptable ester thereof as an active ingredient, in an amount effective for inhibiting growth of human immunodeficient virus and a pharmaceutically acceptable additive.

24. A method for inhibiting growth of human immunodeficient virus, which comprises administering to a patient in need thereof at least one 8-trifluoromethylquinolinecarboxylic acid compound according to claim 1 or a pharmaceutically acceptable salt thereof or a pharmaceutically acceptable ester thereof.

25. The method according to claim 24, wherein the 8-trifluoromethylquinolinecarboxylic acid compound is selected from the group consisting of 1-cyclopropyl-6-fluoro-8-trifluoromethyl-1,4-dihydro-4-oxo-7-[4-(2-pyridyl)piperazin-1-yl]quinoline-3-carboxylic acid, 6-fluoro-8-trifluoromethyl-1,4-dihydro-4-oxo-1-methyl-7-[4-(2-pyrimidinyl)piperazin-1-yl]quinoline-3-carboxylic acid, 6-fluoro-8-trifluoromethyl-1,4-dihydro-4-oxo-1-methyl-7-[4-(2-pyridyl)piperazin-1-yl]quinoline-3-carboxylic acid, a pharmaceutically acceptable salt thereof and a pharmaceutically acceptable ester thereof.

* * * * *